US008614047B2

(12) United States Patent
Ayothi et al.

(10) Patent No.: US 8,614,047 B2
(45) Date of Patent: Dec. 24, 2013

(54) PHOTODECOMPOSABLE BASES AND PHOTORESIST COMPOSITIONS

(75) Inventors: Ramakrishnan Ayothi, San Jose, CA (US); William D. Hinsberg, Fremont, CA (US); Sally A. Swanson, San Jose, CA (US); Gregory M. Wallraff, San Jose, CA (US)

(73) Assignees: International Business Machines Corporation, Armonk, NY (US); JSR Corporation, Tokyo (JP)

( * ) Notice: Subject to any disclaimer, the term of this patent is extended or adjusted under 35 U.S.C. 154(b) by 178 days.

(21) Appl. No.: 13/219,599

(22) Filed: Aug. 26, 2011

(65) Prior Publication Data

US 2013/0052585 A1    Feb. 28, 2013

(51) Int. Cl.
- *C07C 55/02* (2006.01)
- *G03F 7/004* (2006.01)
- *G03F 7/26* (2006.01)

(52) U.S. Cl.
USPC ........ 430/270.1; 430/326; 430/921; 430/925; 562/480

(58) Field of Classification Search
USPC .............. 430/270.1, 326; 562/571, 577, 578, 562/582, 583, 480; 568/18, 24, 34, 35
See application file for complete search history.

(56) References Cited

U.S. PATENT DOCUMENTS

| | | | |
|---|---|---|---|
| 5,663,035 A | 9/1997 | Masuda et al. | |
| 6,365,322 B1 | 4/2002 | Padmanaban et al. | |
| 6,723,483 B1 * | 4/2004 | Oono et al. | 430/170 |
| RE38,980 E | 2/2006 | Thackeray et al. | |
| 7,083,892 B2 | 8/2006 | Takahashi et al. | |
| 7,094,515 B2 | 8/2006 | Kodama | |
| 7,122,294 B2 | 10/2006 | Lamanna et al. | |
| 7,150,949 B2 | 12/2006 | Askebjer et al. | |
| 7,507,518 B2 * | 3/2009 | Fujita et al. | 430/157 |
| 7,718,343 B2 | 5/2010 | Taguchi | |
| 7,824,839 B2 | 11/2010 | Ober et al. | |
| 7,858,289 B2 | 12/2010 | Yamashita | |
| 7,875,415 B2 | 1/2011 | Meagley et al. | |
| 2002/0147259 A1 * | 10/2002 | Namba et al. | 524/377 |
| 2003/0017411 A1 * | 1/2003 | Shimada et al. | 430/270.1 |
| 2004/0033434 A1 * | 2/2004 | Ishihara et al. | 430/270.1 |
| 2004/0137241 A1 * | 7/2004 | Lin et al. | 428/447 |
| 2006/0068318 A1 | 3/2006 | Meagley et al. | |
| 2007/0092829 A1 | 4/2007 | Noelscher et al. | |
| 2007/0117041 A1 | 5/2007 | Noelscher et al. | |
| 2008/0187868 A1 | 8/2008 | Padmanaban et al. | |
| 2009/0023093 A1 * | 1/2009 | Lee et al. | 430/270.1 |
| 2010/0119972 A1 | 5/2010 | Houlihan et al. | |
| 2010/0136477 A1 | 6/2010 | Ng et al. | |
| 2010/0147334 A1 * | 6/2010 | Ogihara et al. | 134/26 |

FOREIGN PATENT DOCUMENTS

| | | |
|---|---|---|
| JP | 4273421 A | 9/1992 |
| JP | 4273422 A | 9/1992 |
| JP | 5299302 A | 11/1993 |
| JP | 6266100 A | 9/1994 |
| JP | 7333851 A | 12/1995 |
| WO | 2010123101 A1 | 10/2010 |

OTHER PUBLICATIONS

Funato et al., Photodecomposable Bases: A Novel Concept to Stabilize Chemically Amplified Resists, J. Photopolym. Sci. Technol. 8(4):543-553 (1995).
Funato et al., Application of Photodecomposable Base Concept to Two-Component Deep-UV Chemically Amplified Resists, SPIE 2724:186-195 (1995).
Houlihan et al., Study of Base Additives for Use in a Single Layer 193 nm Resist Based Upon Poly(norbornene/maleic anhydride/acrylic acid/tert-butyl Acrylate), Proceedings of SPIE 4345:67-77 (2001).
Kruger et al., Fluorinated Acid Amplifiers for EUV Lithography, J. Am. Chem. Soc. 131(29):9862-9863 (2009).
Kruger et al., Fluorinated Acid Amplifiers for EUV Lithography, University of Albany College of Nanoscale Science and Engineering Technical Report, 2009.
Ohshima, Fujifilm: Our Approaches to Optimizing RLS, FujiFilm Technical Report (Oct. 2008).
Padmanaban et al., Sensitized Transparent Photobase Additive for 193 nm Lithography, J. Photopolym. Sci. Technol. 13(4):617-624 (2000).
Przybilla et al., Delay Time Stable Chemically Amplified Deep UV Resist, SPIE 1925:76-91 (1993).
Wang et al., Photobase Generator and Photo Decomposable Quencher for High-Resolution Photoresist Applications, Proc. of SPIE 7639:76390W1-W15 (2010).

* cited by examiner

*Primary Examiner* — Anca Eoff

(74) *Attorney, Agent, or Firm* — Karen Canaan; CanaanLaw, P.C.

(57) ABSTRACT

Provided are novel symmetrical and asymmetrical bifunctional photodecomposable bases (PDBs) with dicarboxylate anion groups that show increased imaging performance. Also provided are photoresist compositions prepared with the bifunctional dicarboxylated PDBs and lithography methods that use the photoresist compositions of the present invention.

29 Claims, 3 Drawing Sheets

Resist G
PHS MAdMA
0.25M TPS PFBS
0.05M BisTPS TFDGA
0.075M PiA Ts
PAB 120C/60s
PEB 115C/60s
Dev 30s Resist H
PHS EAdMA
0.25M TPS PFBS
0.05M BisTPS TFDGA
0.075M PiA Ts
PAB 110C/60s
PEB 110C/60s
Dev 30s Resist I
PHS MAdMA
0.3M TPS PFBS
0.05M BisTPS 2KGA
PAB 120C/60s
PEB 115C/60s
Dev 45s Resist J
PHS MAdMA
0.25M TPS PFBS
0.05M BisTPS 2KGA
PAB 120C/60s
PEB 120C/60s
Dev 45s

PHOTODECOMPOSABLE BASES AND PHOTORESIST COMPOSITIONS

JOINT RESEARCH AGREEMENT

The invention described herein is subject to a joint research agreement between International Business Machines Corporation and JSR Corporation.

TECHNICAL FIELD

The present invention relates generally to photodecomposable bases (PDBs) and photoresist compositions and processes for forming fine patterns on a substrate and/or device. More specifically, the present invention relates to symmetrical and asymmetrical bifunctional PDBs with dicarboxylate anion groups.

BACKGROUND OF THE INVENTION

Photodecomposable bases (PDBs) are photoactive additives used in chemically amplified photoresist formulations to improve photoresist properties and lithographic performance. PDBs are thermally stable basic compounds that produce non-basic products, i.e., neutral or weak acids (pKa 0 to 5), upon exposure to imaging wavelengths. Because effective base concentrations vary with light exposure, the use of PDBs in chemically amplified photoresists offer improved performance, formulation stability, and delay stability over conventional base quencher additives, which are used to control acid diffusion in chemically amplified resists. PDBs have a number of applications in photoresist technology. For example, they are generally added to photoresist compositions to improve resolution, linearity bias, and to stabilize latent images. Examples of PDBs are arylsulfonium or iodonium salts containing anions, such as acetate, hydroxide, or sulfamate.

SUMMARY OF THE INVENTION

The present invention relates to novel bifunctional dicarboxylate anion PDBs, photoresist compositions made from same, and lithographic methods for imaging the photoresist compositions. The photoresist compositions of the present invention are sensitive to exposure radiation and comprise: (a) a polymer; (b) a PDB; (c) a photoacid generator (PAG); and (d) optionally an acid amplifier.

In one aspect of the invention, there is provided a composition comprising at least one dicarboxylate anion photodecomposable base (PDB), wherein the PDB is fluorinated and/or asymmetrical. In one embodiment, the PDB comprises fluorinated bis(triphenylsulfonium) tetrafluorodiglycolic acid (BisTPS TFDGA) and in another embodiment, the PDB comprises asymmetrical bis(triphenylsulfonium) 2-ketoglutaricacid (BisTPS 2KGA).

In a further embodiment of the invention, the at least one PDB is fluorinated and has at least one structure selected from the group consisting of Structures 1, 2, and 5:

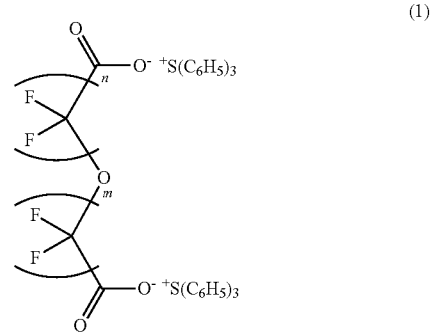

wherein n is 1, 2, or 3 and m is 1, 2, or 3

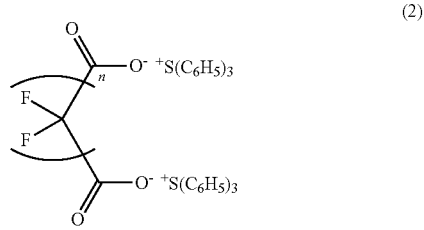

wherein n is 1, 2, or 3

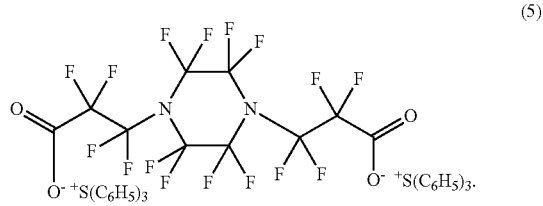

In another embodiment of the invention, the at least one PDB is asymmetrical and has at least one structure selected from the group consisting of Structures 7-10:

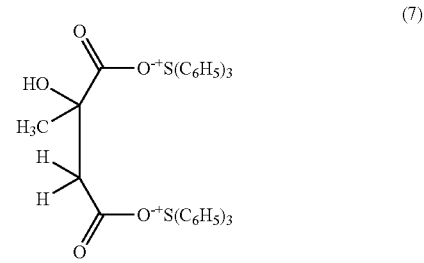

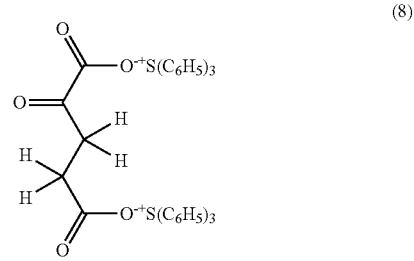

-continued

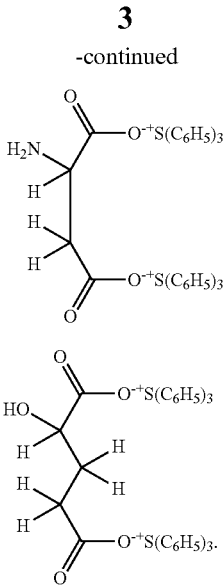

(9)

(10)

In another aspect of the present invention, there is provided a composition comprising at least one dicarboxylate anion PDB having at least one structure selected from the group consisting of Structures 3, 4, and 6:

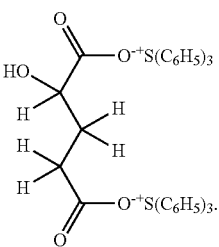

(3)

wherein n is 1, 3, or 4

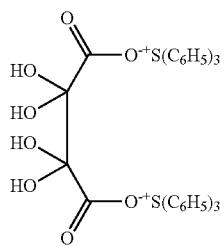

(4)

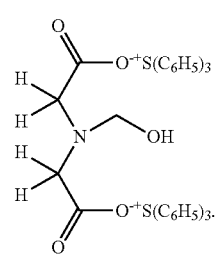

(6)

In a further embodiment of the invention, the at least one PDB-containing composition further comprises a photoresist polymer that may be selected from the group consisting of poly(p-hydroxystyrene)-methyl adamantyl methacrylate (PHS MAdMA) and poly(p-hydroxystyrene)-2-ethyl-2-adamantyl methacrylate (PHS EAdMA).

In another embodiment of the invention, the at least one PDB-containing composition further comprises a PAG that may be selected from the group consisting of sulfonium salts, halonium salts, α,α'-bis-sulfonyl-diazomethanes, trifluoromethanesulfonate esters of imides, trifluoromethanesulfonate esters of hydroxyimides, nitrobenzyl sulfonate esters, sulfonyloxynaphthalimides, pyrogallol derivatives, alkyl disulfones, s-triazine derivatives, and sulfonic acid generators. In a preferred embodiment, the PAG is the sulfonium salt triphenylsulfonium perfluorobutanesulfonate.

In a further embodiment of the invention, the at least one PDB-containing composition further comprises an acid amplifier. In a preferred embodiment, the acid amplifier is pinane acetate p-toluenesulfonate.

In another aspect of the invention, there is provided a method of patterning a substrate comprising the steps of: (a) applying, over a substrate, a photoresist prepared with at least one of the PDB-containing compositions of the present invention, a photoresist polymer, and a PAG; (b) post-application baking of the photoresist; (c) exposing the photoresist to radiation; (d) post-exposure baking of the photoresist; and (e) developing the exposed photoresist with an aqueous base solution. In one embodiment, the photoresist further comprises an acid amplifier. In another embodiment, the acid amplifier is pinane acetate p-toluenesulfonate.

In one embodiment of the invention, the substrate is selected from the group consisting of a metal conductor layer, a ceramic insulator layer, and a semiconductor wafer.

In another embodiment of the invention, the photoresist is exposed with radiation selected from the group consisting of DUV optical radiation, ion-beam projection, x-ray radiation, electron beam (e-beam) radiation, focused beam radiation, and EUV radiation.

Additional aspects and embodiments of the invention will be provided, without limitation, in the detailed description of the invention that is set forth below.

DETAILED DESCRIPTION OF THE INVENTION

Figure 1:
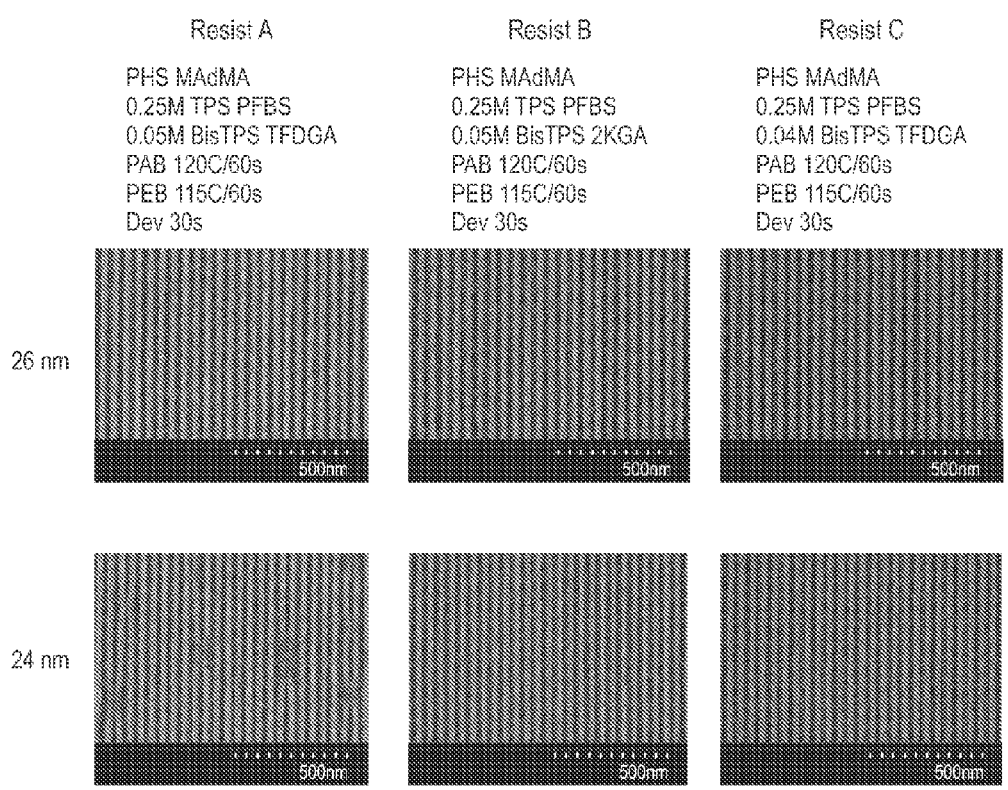
FIG. 1 shows scanning electron microscope (SEM) images at EUV of Resists A-C prepared with the bifunctional dicarboxylate anion PDBs of the present invention, BisTPS TFDGA and BisTPS 2KGA.

Set forth below is a description of what are currently believed to be preferred embodiments of the claimed invention. Any alternates or modifications in function, purpose, or structure are intended to be covered by the claims of this application. As used in this specification and the appended claims, the singular forms "a," "an," and "the" include plural referents unless the context clearly dictates otherwise. The terms "comprises" and/or "comprising," as used in this specification and the appended claims, specify the presence of stated features, integers, steps, operations, elements, and/or components, but do not preclude the presence or addition of one or more other features, integers, steps, operations, elements, components, and/or groups thereof.

The term "monofunctional" is used in its traditional sense to describe an organic compound with a single reactive site.

The term "bifunctional" is used in its traditional sense to describe an organic compound with two reactive sites.

The terms "deep ultraviolet" and "DUV" refer to wavelengths of 300 nm or shorter, with typical DUV exposure wavelengths for lithography techniques being 248 nm (5 eV) with krypton fluoride (KrF) excimer lasers and 193 nm (6.4 eV) with argon fluoride (ArF) excimer lasers. The terms "extreme ultraviolet" or "EUV" refer to wavelengths of 50 nm or shorter, currently expected to be 13.5 nm.

In one embodiment of the invention, there is provided a novel family of bifunctional dicarboxylate anion PDBs, wherein dicarboxylate compounds containing different substituent groups are used to prepare the PDBs. Structures A and B are examples of sulfonium and/or iodonium salt PDBs containing dicarboxylate groups.

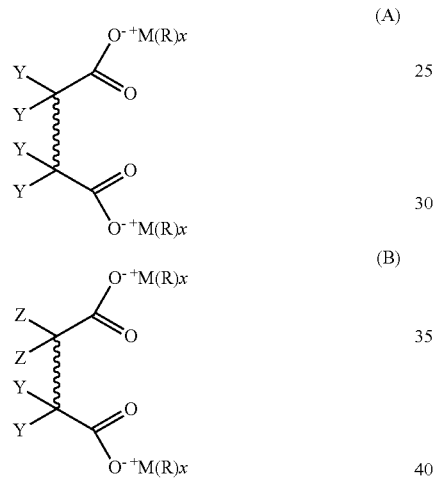

wherein Y and Z are selected from H, C, O, N, P, S, Se, halogens, hydroxyls, carboxyls, amines, alkyls, alkylenes, aryls, and arylenes with the proviso that Y and Z are not the same;

M is selected from S and I;

R is selected from H, hydroxyls, carboxyls, amines, alkyls, alkylenes, aryls, and arylenes; and X=2 when M is I and X=3 when M is S.

Structures 1-10 show specific examples of dicarboxylates that may form the PDBs of Structures A and B. Structures 1-6 are examples of symmetrical dicarboxylate anion PDBs and Structures 7-10 are examples of asymmetrical dicarboxylate anion PDBs. It is to be understood that the compositions of Structures 1, 2, and 3 may include admixtures of the compositions corresponding to different values for m and n. The asymmetrical dicarboxylate anion PDBs allow for the combination of two different carboxylate anion functionalities in one PDB. In other words, the asymmetrical bifunctional PDBs of structures 7-10 allow for the generation of non-basic products with multiple pKas depending on the substituent positioned next to the carboxylate group. The different substituents positioned adjacent to the carboxylate group modify the pKa of the resulting carboxylic acids formed during the photoreaction process.

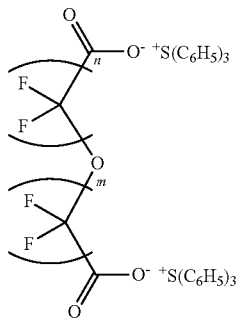

wherein n is 1, 2, or 3 and m is 1, 2, or 3

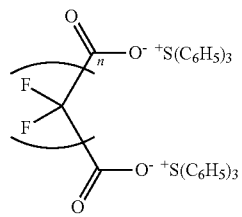

wherein n is 1, 2, or 3

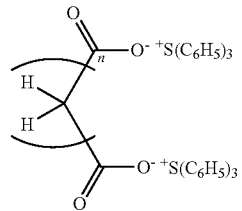

wherein n is 1, 3, or 4

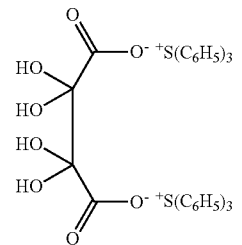

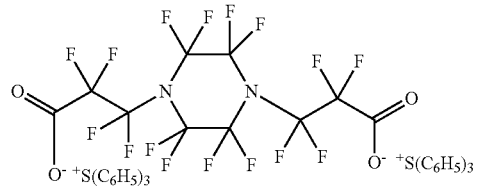

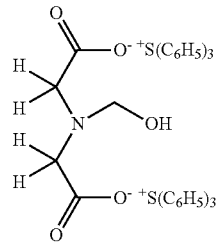

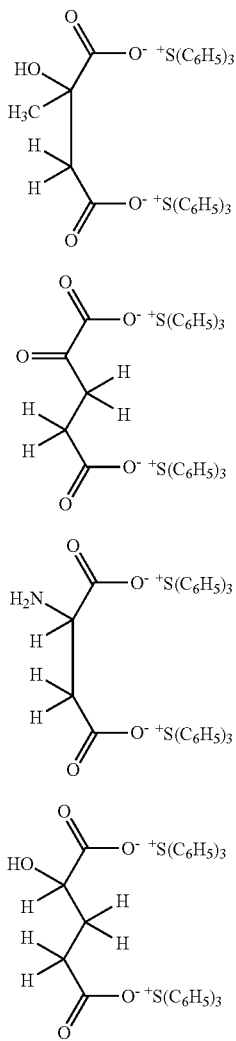

(7)

(8)

(9)

(10)

As previously noted, PDBs are generally added to photoresist compositions to improve resolution, linearity bias, and to stabilize latent images. The novel dicarboxylate anion PDBs of structures 1-10 show the same good or improved lithographic performance as monofunctional PDBs, but require a lower concentration, i.e., about half the amount of monofunctional PDBs to achieve the same or similar lithographic performance (see, Example 7 and FIG. 2).

Following is a description of the synthesis, characterization, and resist processing methods used to prepare photoresist compositions for exposure to EUV lithography using the bifunctional dicarboxylate anion PDBs of the present invention. The following description is merely illustrative and is not meant to limit the synthesis, characterization, photoresist composition, resist processing, and/or exposure limits of the resulting photoresist compositions and/or the PDBs used to prepare the photoresist compositions.

Bifunctional PDBs representing the two families of compounds of Structures A and Structures 1-6, and Structures B and Structures 7-10, respectively, were synthesized and characterized.

Example 1 describes the synthesis and characterization of the symmetric dicarboxylate anion PDB bis-triphenylsulfonium tetrafluorodiglycolic acid (BisTPS TFDGA), which is based upon Structure 1 above and which is shown below as Structure C. Example 2 describes the synthesis and characterization of the asymmetric dicarboxylate anion PDB bis-triphenylsulfonium 2-ketoglutaric acid (BisTPS 2KGA), which is based upon Structure 8 above and which is shown below as Structure D.

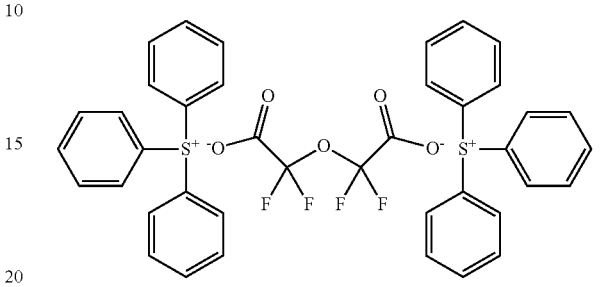

(C)

BisTPS TFDGA (D)

BisTPS 2KGA

Figure 2:
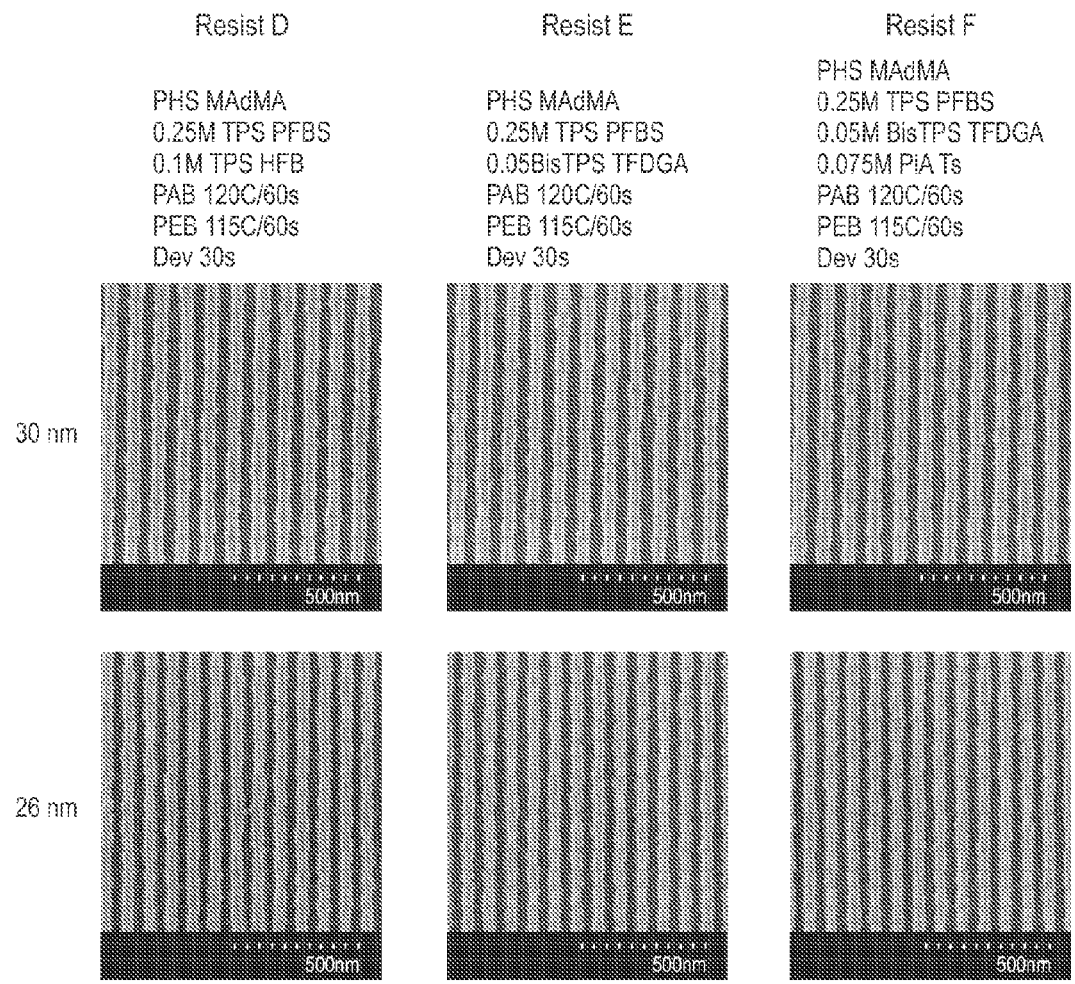
FIG. 2 shows SEM images at EUV of Resists D-F prepared with the monofunctional PDB, TPS HFB, and the bifunctional dicarboxylate anion PDB, BisTPS TFDGA.
Figure 3:
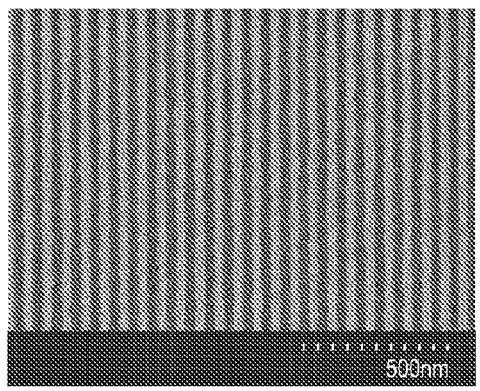
FIG. 3 shows SEM images at EUV of Resists G-J prepared with the bifunctional dicarboxylate anion PDBs of the present invention, BisTPS TFDGA and BisTPS 2KGA.
Figure 3:
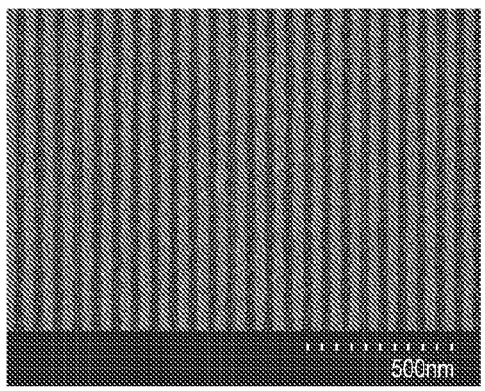
Figure 3:
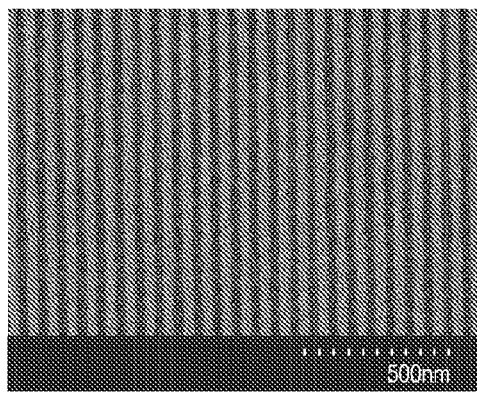
Figure 3:
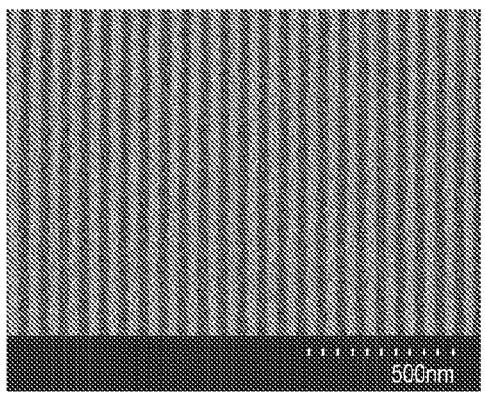

Example 3 describes the synthesis of the monofunctional PDB triphenylsulfoniumheptafluorbutyrate (TPS HFB). Example 4 describes the preparation of 10 different photoresist compositions (Resists A-J) prepared from the PDBs described in Examples 1-3 and Example 5 describes the processing methods used for forming the fine patterns of Resists A-J. As shown in Table 1 of Example 4, Resists A, C, and E-H were prepared with BisTPS TFDGA; Resists B, I, and J were prepared with BisTPS 2KGA; and Resist D was prepared with the TPS HFB. The characteristics of Resists A-J are set forth in Table 2 of Example 5. FIG. 1 shows SEM images at EUV of Resists A-C; FIG. 2 shows SEM images at EUV of Resists D-F; and FIG. 3 shows SEM images at EUV of Resists G-J.

The EUV lithographic performance of the photoresist compositions containing the bifunctional dicarboxylate anion PDBs of the present invention were evaluated in terms of resolution, line edge or width roughness (LER or LWR), and sensitivity (collectively, RLS) (FIG. 1 and Example 6). The RLS and process window performance of photoresist compositions prepared from the bifunctional dicarboxylate anion PDBs of the present invention and standard monofunctional anion PDBs were also evaluated (FIG. 2 and Example 7). In addition, the RLS performance of photoresist compositions containing the bifunctional dicarboxylate PDBs with additives, such as acid amplifiers (FIGS. 2 and 3 and Example 8) and other polymers (FIG. 3 and Example 9), was also investigated.

In another embodiment of the invention, there is provided a photoresist composition prepared from the bifunctional dicarboxylate anion PDBs of the present invention. A photoresist is a light-sensitive material typically used in industrial processes, such as photolithography and photoengraving to form a patterned coating on a surface. Photoresists are classified into two groups: positive resists and negative resists. A positive resist is a photoresist in which the portion of the photoresist that is exposed to light becomes soluble to the photoresist developer and the portion of the photoresist that is unexposed remains insoluble to the photoresist developer. A negative resist is a photoresist in which the portion of the photoresist that is exposed to light becomes insoluble to the photoresist developer and the unexposed portion of the photoresist is dissolved by the photoresist developer.

The PDB-containing photoresist compositions of the present invention will typically include one or more photoresist polymers or copolymers, which may be base soluble or insoluble. As is known to those of skill in the art, photoresist polymers or copolymers with acid labile groups are insoluble in aqueous base solution, but in the presence of an acid, the polymers are catalytically deprotected such that they become soluble in an aqueous base solution.

Examples of photoresist polymers that may be used to prepare the PDB-containing photoresists of the present invention include without limitation, aromatic polymers, such as homopolymers or copolymers of hydroxystyrene protected with an acid labile group; acrylates, such as for example, poly(meth)acrylates with at least one unit containing a pendant alicyclic group, and with the acid labile group being pendant from the polymer backbone and/or from the aclicyclic group; cycloolefin polymers; cycloolefin maleic anhydride copolymers; cycloolefin vinyl ether copolymers; siloxanes; silsesquioxanes; carbosilanes; and oligomers, including polyhedral oligomeric silsesquioxanes, carbohydrates, and other cage compounds. The foregoing polymers or oligomers are appropriately functionalized with aqueous base soluble groups, acid-labile groups, polar functionalities, and silicon containing groups as needed.

Examples of photoresist copolymers that may be used with the PDB-containing photoresist compositions of the present invention include without limitation poly(p-hydroxystyrene)-methyl adamantyl methacrylate (PHS-MAdMA), polyp-hydroxystyrene)-2-ethyl-2-adamantyl methacrylate (PHS-EAdMA), poly(p-hydroxystyrene)-2-ethyl-2-cyclopentyl methacrylate (PHS-ECpMA), poly(p-hydroxystyrene)-2-methyl-2-cyclopentyl methacrylate (PHS-MCpMA).

In addition to the foregoing, low molecular weight amorphous glass forming materials (or molecular glass) [MW<3000 Da] are being considered as alternative choices to polymeric resists for next generation photoresist design (*Journal of Material Chemistry* 16:1693 (2006)); accordingly, molecular glass materials derived from low molecular weight phenolic compounds and cyclodextrin may also be prepared from the bifunctional PDBs of the present invention. Examples of low molecular weight amorphous glass forming materials include without limitation, partially protected NORIA molecular glass (NORIA-AD; *Journal of Material Chemistry* 20:4445 (2010)).

In another embodiment of the invention, the PDB-containing photoresist compositions of the present invention may include one or more photoacid generators (PAGs). A PAG is capable of releasing or generating acid upon exposure to radiation. Typical PAGs include, without limitation: (1) sulfonium salts, such as triphenylsulfonium perfluorobutanesulfonate (TPS PFBS), triphenylsulfonium perfluoromethanesulfonate (triphenylsulfonium triflate), triphenylsulfonium perfluoropentane-sulfonate, triphenylsulfonium hexafluoroantimonate, triphenylsulfonium hexafluoro arsenate, triphenylsulfonium hexafluorophosphate, triphenylsulfonium bromide, triphenylsulfonium chloride, triphenylsulfonium iodide, 2,4,6-trimethylphenyldiphenylsulfonium perfluoro-butanesulfonate, 2,4,6-trimethylphenyldiphenylsulfonium benzenesulfonate, diphenylethylsulfonium chloride, and phenacyldimethylsulfonium chloride; (2) halonium salts, particularly iodonium salts, including diphenyliodonium perfluoromethanesulfonate (diphenyliodonium triflate), diphenyliodonium perfluorobutanesulfonate, diphenyliodonium perfluoropentane-sulfonate, diphenyliodonium hexafluoroantimonate, diphenyliodonium hexafluoroarsenate, bis-(t-butylphenyl)-iodonium triflate, and bis-(t-butylphenyl)-iodonium camphanylsulfonate; (3) α,α'-bis-sulfonyl-diazomethanes such as bis(p-toluenesulfonyl)diazomethane, methylsulfonyl p-toluenesulfonyldiazomethane, 1-cyclohexylsulfonyl-1-(1,1-dimethylethylsulfonyl)diazomethane, and bis(cyclohexylsulfonyl)diazomethane; (4) trifluoromethanesulfonate esters of imides and hydroxyimides, e.g., α-(trifluoromethylsulfonyloxy)-bicyclo[2.2.1]hept-5-ene-2,3-dicarboximide (MDT); (5) nitrobenzyl sulfonate esters such as 2-nitrobenzyl p-toluenesulfonate, 2,6dinitrobenzyl p-toluenesulfonate, and 2,4-dinitrobenzyl p-trifluoromethylbenzene sulfonate; (6) sulfonyloxynaphthalimides such as N-camphorsulfonyloxynaphthalimide and N-pentafluorophenylsulfonyloxynaphthalimide; (7) pyrogallol derivatives (e.g., trimesylate of pyrogallol); (8) naphthoquinone-4-diazides; (9) alkyl disulfones; (10) s-triazine derivatives; and (11) miscellaneous sulfonic acid generators including t-butylphenyl-α-(p-toluenesulfonyloxy)-acetate, t-butyl-α-(p-toluenesulfonyloxy) acetate, and N-hydroxynaphthalimide dodecane sulfonate (DDSN), and benzoin tosylate.

Other suitable PAGs are disclosed in Reichmanis et al., *Chemistry of Materials* 3:395 (1991) and in U.S. Pat. No. 5,679,495 to Yamachika et al. Additional suitable PAGs useful in conjunction with the compositions and methods provided herein will be known to those skilled in the art and/or are described in the pertinent literature.

In a further embodiment of the invention, the PDB-containing photoresist compositions of the present invention may include one or more acid amplifiers. An acid amplifier is a compound that is decomposed with an acid to generate an acid. Examples of acid amplifiers include without limitation, pinane acetate p-toluenesulfonate (PiA Ts), tert-butyl-2-methyl-2-tosyloxymethyl acetoacetate, and 2-phenyl-2-(2-tosyloxyethyl)-1,3-dioxolane. Other acid amplifiers are referenced in the literature at *J. Photopolym. Sci. and Tech.* 8:43-46 (1995) and *J. Photopolym. Sci. and Tech.* 9: 29-30 (1996).

The bifunctional PDB compounds and the PDB-containing photoresist compositions of the present invention find utility in a number of applications with one preferred application being lithography for the manufacture of integrated circuits on semiconductor substrates. Such lithographic processes include, without limitation, the formation of patterned material features and/or layer structures on a substrate surface, such as for example, metal wiring lines, holes for contacts or vias, insulation sections (e.g., damascene trenches or shallow trench isolation), trenches for capacitor structures, and ion implanted semiconductor structures for transistors. Examples of substrate surfaces that may be used with the bifunctional PDB compounds and PDB-containing photoresist compositions of the present invention include without limitation, metal conductor layers, ceramic insulator layers, and semiconductor wafers. It is to be understood that other substrate surfaces may be used and that materials for use with such other substrate surfaces will depend upon the stage of the manufacturing process and the desired material set for the end product.

An exemplary microlithographic method for patterning a substrate with a bifunctional PDB-containing photoresist of the present invention includes the following steps:

(a) applying a PDB-containing photoresist onto a substrate;
(b) post-application baking (PAB) of the photoresist;
(b) exposing the photoresist;
(c) post-exposure baking (PEB) of the photoresist; and
(d) developing the exposed resist with an aqueous base solution.

Exposure of the photoresist may occur by any suitable method including without limitation, DUV optical radiation, ion-beam projection, x-ray radiation, electron beam (e-beam) radiation, focused beam radiation, and EUV radiation. The PDB-containing photoresists of the present invention may also be used for mixed lithography processes wherein more than one exposure method is used, such as for example, e-beam and EUV radiation.

After exposure, the photoresist structure with the desired pattern is obtained (developed) by contacting the photoresist layer with an aqueous alkaline solution, which selectively dissolves the areas of the photoresist that were exposed to radiation in the case of a positive photoresist, or the unexposed areas in the case of a negative photoresist. Some aqueous alkaline solutions (developers) comprise aqueous solutions of tetramethyl ammonium hydroxide. The resulting lithographic structure on the substrate is then typically dried to remove any remaining developer. If a top coat has been used, it can be dissolved by the developer in this step.

It is to be understood by those of skill in the art that the PAB and PEB of the method of the present invention will vary with the materials and radiation that are used to carry out the method. For EUV exposure, typical PAB and PEB temperatures and bake times range from 50° C. to 150° C. for 30 to 200 seconds, with preferred temperatures and bake times ranging from 100 to 130° C. for 60 to 120 seconds. PAB temperatures will sometimes, but not necessarily, be higher than PEB temperatures and PEB bake times will sometimes, but not necessarily, be longer than PAB back times. Example 9 and FIG. 3 describe an experiment where Resist B is subjected to a higher PEB and processing time and named Resist J (see, Tables 1 and 2). As shown in Table 2, Resist B was subjected to a PEB of 115° C. for 60 seconds and Resist J was subjected to a PEB of 120° C. for 60 seconds. Table 3 demonstrates that increased PEB conditions may improve the resolution at EUV wavelengths (compare Resist B to Resist J).

Due to its significantly shorter wavelength, EUV lithography at 13.5 nm is considered to be the promising technology for next generation lithography, which includes EUV lithography, x-ray lithography, e-beam lithography and focused ion beam lithography. It should be understood that the invention is not limited to any specific lithographic process and that the PDBs and PDB-containing photoresists of the present invention are intended to be used with any suitable lithographic imaging technique.

It is to be understood that while the invention has been described in conjunction with the embodiments set forth above, the foregoing description as well as the examples that follow are intended to illustrate and not limit the scope of the invention. Further, it is to be understood that the embodiments and examples set forth herein are not exhaustive and that modifications and variations of the invention will be apparent to those of ordinary skill in the art without departing from the scope and spirit of the invention.

All patents and publications mentioned herein are incorporated by reference in their entireties.

EXPERIMENTAL

The following examples are set forth to provide those of ordinary skill in the art with a complete disclosure of how to make and use the aspects and embodiments of the invention as set forth herein. While efforts have been made to ensure accuracy with respect to variables such as amounts, temperature, etc., experimental error and deviations should be taken into account. Unless indicated otherwise, parts are parts by weight, temperature is degrees centigrade, and pressure is at or near atmospheric. All components were obtained commercially unless otherwise indicated.

The structure, composition, and molecular weight of the resist polymers used to prepare the PDB resist compositions described in the Examples are shown below.

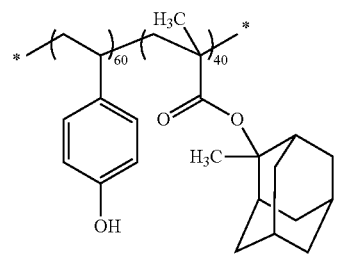

PHS-MAdMA
MW = 8.99 kDa; Mn = 5.46 kDa

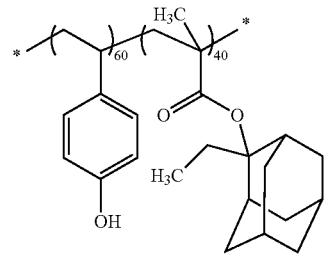

PHS-EAdMA
MW = 7.34 kDa; Mn = 4.06 kDa

The acid amplifier, pinane acetate tosylate (PiATs) that was used in the Examples was synthesized from pinane tosylate (PiTs). A description of the procedures used to synthesize PiTs and PiATs follow. All chemicals were received from commercial source and used as received. NMR spectra were recorded using 400 MHz Bruker Avance Spectrometer (Bruker-Biospin, Billerica, Mass.).

Synthesis of PiTs:

PiTs was synthesized as described in Hirata et al., *J. Org. Chem* 36:412 (1971).

(1S,2S,3R,5S)-(+)-Pinanediol (3.61 g, 21.2 mmol) and 20 mL anhydrous pyridine were placed in a 50 mL round bottomed flask and stirred under nitrogen. Next, p-Toluenesulfonyl chloride (4.45 g, 23.3 mmol) was added to the mixture, which was stirred overnight at room temperature. The reaction mixture was poured into 200 mL deionized water and the product was extracted into ethyl acetate (3×75 mL). The combined organic layers were quickly washed with 10% hydrochloric acid (3×), deionized water (2×), saturated aqueous sodium bicarbonate, and brine and then dried over anhydrous magnesium sulfate. After filtering, 5 g of basic alumina was added and the slurry was stirred for 1 hour. The alumina was removed by filtration and the solution was rotary evaporated to dryness to yield 6.38 g of crystals (93% yield) of pinane tosylate (PiTs). $^1$H-NMR (CDCl$_3$) (δ, ppm): 7.86 (d, 2H, ArH), 7.39 (d, 2H, ArH), 4.92-4.87 (m, 1H, CH—OTs), 2.48 (s, 3H, CH$_3$), 2.28-2.21 (m, 2H, C—H), 2.02 (m, 1H, C—H), 1.91 (m, 1H, C—H), 1.83 (m, 1H, C—H), 1.56 (m, 2H, CH), 1.28 (s, 3H, CH$_3$), 1.23 (s, 3H, CH$_3$), 0.94 (s, 3H, CH$_3$).

Synthesis of PiATs:

The acetate derivative of PiTs was synthesized based on the procedures set forth in Kruger et al., *J. Am. Chem. Soc.* 131: 9862 (2009), but scandium triflate was used instead of cobalt chloride as the acylation catalyst per Ishihara et al., *J. Am. Chem. Soc.* 117:4413 (1995).

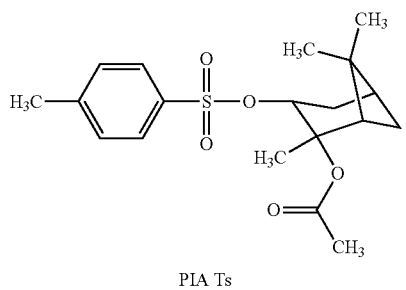 [SMILES: CC(=O)OC1(C)C(OS(=O)(=O)c2ccc(C)cc2)CC2CC1C2(C)C ; "PIA Ts"]

PIA Ts

PiTs (6.33 g, 19.51 mmol), acetic anhydride (9.96 g, 97.55 mmol), scandium triflate (96 mg, 0.195 mmol), and 150 mL acetonitrile were placed in a 500 mL round bottomed flask and stirred at room temperature under nitrogen for 3 days. Water (250 mL) was added and the product was extracted into ethyl acetate (3×100 mL). The combined organic layers were washed with saturated sodium bicarbonate solution, deionized water, and brine and dried over magnesium sulfate, filtered, and rotary evaporated to dryness to yield 7.33 g of wet crystals of a mixture of PiATs and PiTs (determined by comparing the integrals of the proton NMR peaks at 4.9 and 2.9 ppm which should be equivalent in the pure product). The mixture was redissolved in 150 mL acetonitrile and treated again with 9.96 g acetic anhydride and 96 mg scandium triflate for another 2 days. The resulting 7.01 g of crystals had a melting point of ~65° C. and a yield of 98%. $^1$H-NMR (CDCl$_3$) (δ, ppm): 7.86 (d, 2H, ArH), 7.37 (d, 2H, ArH), 4.93-4.89 (dd, 1H, CH-OTs), 2.91 (t, 1H, CH), 2.24 (s, 3H, acetate CH$_3$), 2.28-2.21 (m, 1H, CH), 1.97 (s, 3H, CH$_3$), 1.96-1.89 (m, 2H, CH), 1.64 (s, 1H, CH), 1.46 (s, 3H, CH$_3$), 1.34-1.28 (m, 1H, CH), 1.23 (s, 3H, CH$_3$), 0.98 (s, 3H, CH$_3$).

Tetrafluorodiglycolic acid disodium salt (Synquest Laboratories, Alachua, Fla.), silver heptafluorobutyrate (Sigma-Aldrich, St. Louis, Mo.), 2-ketoglutaric acid disodium salt or disodium 2-oxoglutarte (TCI America, Portland, Oreg.) and triphenylsulfonium bromide (TCI America, Portland, Oreg.) was purchased and used as received. NMR spectra were recorded using 400 MHz Bruker Avance Spectrometer (Bruker-Biospin, Billerica, Mass.).

Example 1

Synthesis of Bis(Triphenylsulfonium) Tetrafluorodiglycolic Acid [BisTPS TFDGA]

Tetrafluorodiglycolic acid disodium salt (0.45 g, 1.8 mmol) was dissolved in 6 mL of water and added slowly to a solution of triphenylsulfonium bromide (1.25 g, 3.6 mmol, dissolved in 12 mL dichloromethane). The mixture was stirred overnight at room temperature. The reaction mixture was evaporated to dryness (or to an oil stage) on a rotary evaporator. The product obtained from evaporation was washed with ethyl ether and dissolved using an excess amount of dichloromethane and filtered. After the evaporation of dichloromethane, the pure compound was obtained as a white solid.

Results: Yield=~75%. $^1$H NMR (CDCl$_3$) (δ, ppm): 7.6-7.95 (m, (C$_6$H$_5$)$_3$S$^+$); $^{19}$F NMR (CDCl$_3$; CF$_3$COOH) (δ, ppm); −75.68 (t, —CF$_2$—O—CF$_2$—)

Example 2

Synthesis of Bis(Triphenylsulfonium) 2-Ketoglutaricacid [BisTPS 2KGA]

2-ketoglutaric acid disodium salt (0.4 g, 2.1 mmol) was dissolved in 6 mL of water. Triphenylsulfonium bromide (1.4 g, 4.1 mmol) was dissolved in 12 mL dichloromethane. The salt solution was added dropwise to the triphenylsulfonium bromide solution and the mixture was stirred overnight at room temperature. The reaction mixture was evaporated to dryness (or on oil stage) on a rotary evaporator. The product obtained from evaporation was washed with ethyl ether and dissolved using an excess amount of dichloromethane and filtered. After the evaporation of dichloromethane, the pure compound was obtained as a white solid.

Results: Yield=~75%. $^1$H NMR (CDCl$_3$) (δ, ppm): 7.6-7.95 (m, (C$_6$H$_5$)$_3$S$^+$), 2-2.25 (—CH$_2$—CH$_2$—).

Example 3

Synthesis of Monofunctional PDB Triphenylsulfonium Heptafluorobutyrate [TPS HFB]

Silver heptafluorobutyrate (0.5 g, 1.5 mmol) was dissolved in 25 mL of water. Triphenylsulfonium bromide (0.5 g, 1.6 mmol) was dissolved in 50 mL dichloromethane. The salt solution was added dropwise to the triphenylsulfonium bromide solution and the mixture was stirred overnight at room temperature. The dichloromethane layer was separated using excess dichloromethane and the dichloromethane layer was evaporated to dryness (or on oil stage) on a rotary evaporator. The product obtained from evaporation was washed with ethyl ether. The product obtained was dissolved using an excess amount of dichloromethane and precipitated using ethyl ether. The mixture was filtered and recovered precipitate was dried. The pure compound was obtained as a white solid.

Results: Yield=~65%. $^1$H NMR (CDCl$_3$) (δ, ppm): 7.6-7.9 (m, (C$_6$H$_5$)$_3$S$^+$); $^{19}$F NMR (CDCl$_3$; CF$_3$COOH) (δ, ppm); −80.7 (CF$_3$—), −117.6 (—CF$_2$—COO$^-$), −126.7 (—CF$_2$—CF$_2$—COO$^-$).

Example 4

Preparation of Resist Compositions

Several resist compositions were prepared in a mixture of propylene glycol methyl ether acetate (PGMEA)/ethyl lactate solvent (30:70 wt %) containing resin or polymer and PAG to yield a loading of 0.25 to 0.3 moles/kg solids in the coated film. PDB concentrations in the films ranged from 0.1-0.05 moles/kg solids. Typical acid amplifier loadings were approximately 0.075 moles/kg solids. Evaluation of the resist composition prepared as set forth herein is summarized in Table 1. AA=Acid Amplifier; PHS-MAdMA=poly(p-hydroxystyrene)-methyl adamantyl methacrylate; PHS-EAdMA=poly(p-hydroxystyrene)-ethyl adamantyl methacrylate; TPS PFBS=triphenylsulfonium perfluorobutanesulfonate; PiA Ts=pinane acetate p-toluenesulfonate.

TABLE 1

| Resist | Polymer | PAG | PDB | AA | Remarks |
|---|---|---|---|---|---|
| Resist A | PHS MAdMA | TPS PFBS (0.25M) | BisTPS TFDGA (0.05M) | None | Bifunctional PDB 1 formulation. |
| Resist B | PHS MAdMA | TPS PFBS (0.25M) | BisTPS 2KGA (0.05M) | None | Bifunctional PDB 2 formulation. |
| Resist C | PHS MAdMA | TPS PFBS (0.25M) | BisTPS TFDGA (0.04M) | None | Bifunctional PDB 1 formulation with lower PDB concentration. Compare Resists A vs. C. |
| Resist D | PHS MAdMA | TPS PFBS (0.25M) | TPS HFB (0.1M) | None | Monofunctional PDB formulation |
| Resist E | PHS MAdMA | TPS PFBS (0.25M) | BisTPS TFDGA (0.05M) | None | Bifunctional PDB 1 formation for comparison. Compare Resist D vs. E. |
| Resist F | PHS MAdMA | TPS PFBS (0.25M) | BisTPS TFDGA (0.05M) | PiA Ts (0.075M) | Bifunctional PDB 1 plus AA formulation. |
| Resist G | PHS MAdMA | TPS PFBS (0.25M) | BisTPS TFDGA (0.05M) | PiA Ts (0.075M) | Bifunctional PDB 1 plus AA formulation for comparison. Compare Resist B vs. H. |
| Resist H | PHS EAdMA | TPS PFBS (0.25M) | BisTPS TFDGA (0.05M) | PiA Ts (0.075M) | Bifunctional PDB 1 plus AA formulation with different polymer. |
| Resist I | PHS MAdMA | TPS PFBS (0.3M) | BisTPS 2KGA (0.05M) | None | Bifunctional PDB 2 formulation with different PAG loading. Compare Resist B vs. I. |
| Resist J | PHS MAdMA | TPS PFBS (0.25M) | BisTPS 2KGA (0.05M) | None | Bifunctional PDB 2 formulation plus different resist processing step. Compare Resist B vs. J. |

Example 5

Processing of Resist Compositions

The resist compositions of Example 4 were processed as follows. 40 nm thick films were prepared by spincoating onto a bottom anti-reflective coating (BARC) coated substrate (DUV42P, Brewer Science, Inc., Rolla, Mo., or NCX-011, Nissan Chemical Industries, Ltd., Tokyo, Japan) and post applied baked (PAB) at 110 or 120° C. for 60 seconds. EUV exposures were carried out on similar EUV microfield exposure tools (MET) at either Lawrence Berkeley National Laboratory or Albany Nanotech. The imaging wavelength was nation to EUV. Berkeley MET exposure was performed using rotated dipole illumination. Albany e-MET exposure was performed using Quadrapole illumination. Lithographic RLS performance of both illumination is comparable but Berkeley MET shows higher resolution (smaller critical dimension 13.5 nm with a numerical aperture (NA) of 0.30 with illumination (CD)). The films were post-exposure baked (PEB) at 110 or 115 or 120° C. for 60 seconds. After PEB, the films were developed using 0.26 N tetramethylammonium hydroxide (TMAH) solution for several seconds (30 or 45 s). Top-down images, CD (resist line size) and line width roughness (LWR) for resist D-F were obtained using critical dimension scanning electron microscopy (CD-SEM). Top-down images for resist A-C and G-J were obtained using field emission scanning electron microscopy. CD and line edge roughness (LER) for resist A-C and G-J were determined using SuMMIT (Stochastic LER Toolbox, EUV Technology, Martinez, Calif.). Table 2 sets forth the processing conditions for Resists A-J. FT=Film Thickness.

TABLE 2

| Resist | Substrate | PAB (° C.) 60 s | FT (nm) | EUV Exposure | PEB (° C.) 60 s | Dev (s) |
|---|---|---|---|---|---|---|
| Resist A | DUV 42P (63 nm) | 120 | 40 | Berkeley MET (NA - 0.3; Rotated Dipole) | 115 | 30 |
| Resist B | DUV 42P (63 nm) | 120 | 40 | Berkeley MET (NA - 0.3; Rotated Dipole) | 115 | 30 |
| Resist C | DUV 42P (63 nm) | 120 | 40 | Berkeley MET (NA - 0.3; Rotated Dipole) | 115 | 30 |
| Resist D | NCX-011 (20 nm) | 120 | 40 | Albany e-MET (NA - 0.3; Quadrapole) | 115 | 30 |
| Resist E | NCX-011 (20 nm) | 120 | 40 | Albany e-MET (NA - 0.3; Quadrapole) | 115 | 30 |
| Resist F | NCX-011 (20 nm) | 120 | 40 | Albany e-MET (NA - 0.3; Quadrapole) | 115 | 30 |
| Resist G | DUV 42P (63 nm) | 120 | 40 | Berkeley MET (NA - 0.3; Rotated Dipole) | 115 | 30 |
| Resist H | DUV 42P (63 nm) | 110 | 40 | Berkeley MET (NA - 0.3; Rotated Dipole) | 110 | 30 |

TABLE 2-continued

| Resist | Substrate | PAB (° C.) 60 s | FT (nm) | EUV Exposure | PEB (° C.) 60 s | Dev (s) |
|---|---|---|---|---|---|---|
| Resist I | DUV 42P (63 nm) | 120 | 40 | Berkeley MET (NA - 0.3; Rotated Dipole) | 115 | 45 |
| Resist J | DUV 42P (63 nm) | 120 | 40 | Berkeley MET (NA - 0.3; Rotated Dipole) | 120 | 45 |

Example 6

Lithography Performance of Bifunctional Dicarboxylate Anion PDB

Photoresist formulations A-C from Example 4 containing the bifunctional dicarboxylate anion PDBs, BisTPS TFDGA and BisTPS 2KGA, were prepared and evaluated at EUV. EUV resolution, line edge roughness (LER), and sensitivity (RLS) performance of Resists A-C is shown in FIG. 1. As shown therein, the BisTPS TFDGA PDB at 0.05M (Resist A) and the BisTPS TFDGA PDB at 0.04 M (Resist C) as well as the BisTPS 2KGA PDB at 0.05M (Resist B) resolved 26 nm line and space (LS) patterns. Resist B also resolved 24 nm LS patterns. While Resist A showed pattern collapse at 24 nm LS patterns, the collapse was resolved by optimizing the BisTPS TFDGA loading in the resist composition (to 0.04M) thus resulting in the resolution of 24 nm LS patterns (Resist C).

Processing Conditions: Substrate=BARC; FT=40 nm; PAB=120 C/60 s; Exposure=EUV (Rotated Dipole); PEB=115° C./60 s; Dev=30 s.

Example 7

Lithography Performance of Bifunctional Dicarboxylate Anion PDB Versus Monofunctional PDB The bifunctional dicarboxylate anion PDBs were compared to standard monofunctional PDBs in photoresist formulations. Photoresist formulations from Example 4 containing either the standard PDB triphenylsulfonium heptafluorobutyrate TPS HFB (Resist D) or the bifunctional dicarboxylate anion PDB BisTPS TFDGA (Resists E and F) were evaluated at EUV. EUV RLS performance of Resists D-F is shown in FIG. 2. As shown therein, Resists D, E, and F resolved 30 and 26 nm LS patterns. The bifunctional PDBs (Resists E and F), however, had a wider process window, i.e., exposure latitude (EL) and depth of focus (DOF), than the monofunctional PDB (Resist D) (see, Table 3). The bifunctional PDBs were used at half the concentration (0.05 M) of the monofunctional PDB (0.1M) in the photoresist composition. New bifunctional PDBs (Resists E and F) showed good lithographic performance and a better process window than monofunctional PDB (Resist D) at half the concentration.

Processing Conditions: Substrate=BARC; FT=40 nm; PAB=120° C./60 s; Exposure=EUV (Quadrapole); PEB=115° C./60 s; Dev=30 s.

Example 8

Lithography Performance of Bifunctional Dicarboxylate Anion PDB with Acid Amplifier Photoresist formulations with bifunctional dicarboxylate anion BisTPS TFDGA PDB, both without (Resist E) and with (Resist F) pinane acetate p-toluenesulfonate (PiA Ts) as an acid amplifier (AA) were prepared and evaluated at EUV. Both photoresist formulations resolved 30 and 26 nm LS patterns (FIG. 2); however, the AA containing formulation (Resist F) showed better than a 9% improvement in photospeed (Es) over Resist E as well as good RLS performance (Table 3).

Processing Conditions: Substrate=BARC; FT=40 nm; PAB=120° C./60 s; Exposure=EUV (Quadrapole); PEB=115° C./60 s; Dev=30 s.

Example 9

Lithography Performance of Bifunctional Dicarboxylate Anion PDB with Different Polymer and Processing Conditions Resist G was prepared with poly(p-hydroxystyrene)-methyl adamantyl methacrylate (PHS MAdMA) polymer; 0.25 M of the PAG triphenylsulfonium perfluorobutanesulfonate (TPS PFBS); 0.05 M of the bifunctional dicarboxylate anion PDB BisTPS TFDGA; and 0.075 M of the AA PiA Ts. Resist H was prepared with poly(p-hydroxystyrene)-2-ethyl-2-adamantyl methacrylate (PHS EAdMA) polymer; 0.25 M TPS PFBS; 0.05 M of BisTPS TFDGA; and 0.075 M of the AA PiA Ts. Resist I was prepared with PHS MAdMA; increased PAG at 0.3 M TPS PFBS; 0.05 M of the bifunctional dicarboxylate anion PDB BisTPS 2KGA; and no AA. Resist J was prepared with PHS MAdMA; 0.25 M TPS PFBS; 0.05 M BisTPS 2KGA; and no AA (Table 1). Resist H was processed at a lower PAB and PEB temperature (PAB and PEB=110° C.) and showed a lower photospeed (Es) than the other resists due to the presence of the low activation energy protecting group on the PHS EAdMA resist polymer. Resist J, which is similar to Resist B, was exposed at EUV and processed at different PEB conditions (i.e., a higher PEB and longer development time). EUV RLS performance of Resists G-J is shown in FIG. 3.

Processing conditions: Substrate=BARC (bottom anti-reflective coating); FT=40 nm; PAB=120 or 110° C./60 s; Exposure=EUV (Rotated Dipole); PEB=110 or 115 or 120° C./60 s; Dev=30 s or 45 s.

Table 3 summarizes the characteristics of Resists A-J from Examples 6-9. CD (critical dimension)=resist line size; LER=line edge roughness; Es=photospeed; LWR=line width roughness; EL=exposure latitude; DOF=depth of focus.

TABLE 3

|  | CD (nm) | LER (nm) | Es (mJ/cm$^2$) | LWR (nm) | EL (%) | DOF (nm) |
|---|---|---|---|---|---|---|
| Resist A 26 nm | 26.9 | 4.0 | 25.0 | | | |
| Resist A 24 nm | 25.0 | — | 25.0 | | | |
| Resist B 26 nm | 26.7 | 4.0 | 24.0 | | | |
| Resist B 24 nm | 23.2 | 4.1 | 24.0 | | | |

TABLE 3-continued

| | CD (nm) | LER (nm) | Es (mJ/cm$^2$) | LWR (nm) | EL (%) | DOF (nm) |
|---|---|---|---|---|---|---|
| Resist C 26 nm | 26.8 | 4.1 | 24.0 | | | |
| Resist C 24 nm | 25.3 | 3.9 | 24.0 | | | |
| Resist D 30 nm | 30.7 | | 23.75 | 5.4 | 7 | 300 |
| Resist D 26 nm | 27.7 | | 23.75 | 5.5 | 0 | 200 |
| Resist E 30 nm | 30.7 | | 26.5 | 5.2 | 9.8 | 350 |
| Resist E 26 nm | 26.0 | | 26.5 | 4.9 | 9.5 | 350 |
| Resist F 30 nm | 30.6 | | 24.22 | 5.6 | 9.0 | 400 |
| Resist F 26 nm | 27.0 | | 24.22 | 5.4 | 9.2 | 300 |
| Resist G 26 nm | 24.8 | 3.7 | 23.0 | | | |
| Resist H 26 nm | 26.7 | 4.2 | 20.0 | | | |
| Resist I 26 nm | 26.1 | 4.0 | 22.0 | | | |
| Resist J 26 nm | 26.3 | 3.3 | 23.0 | | | |

We claim:

1. A composition comprising at least one dicarboxylate anion photodecomposable base (PDB), a resist polymer, and pinane acetate p-toluenesulfonate as an acid amplifier, wherein the PDB is fluorinated and/or asymmetrical.

2. The composition of claim 1, wherein the at least one PDB comprises bis(triphenylsulfonium) tetrafluorodiglycolic acid (BisTPS TFDGA).

3. The composition of claim 1, wherein the at least one PDB comprises bis(triphenylsulfonium) 2-ketoglutaricacid (BisTPS 2KGA).

4. The composition of claim 1, wherein the at least one PDB is fluorinated and has at least one structure selected from the group consisting of Structures 1, 2, and 5:

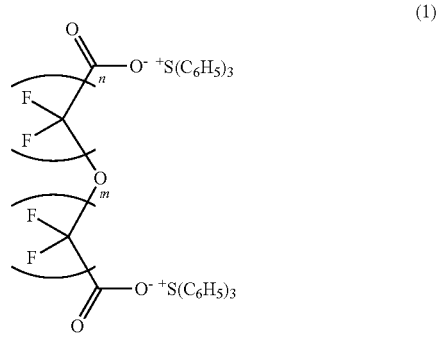

wherein n is 1, 2, or 3 and m is 1, 2, or 3

(1)

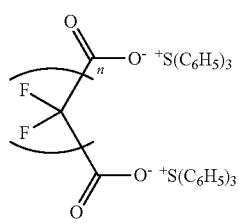

wherein n is 1, 2, or 3

(2)

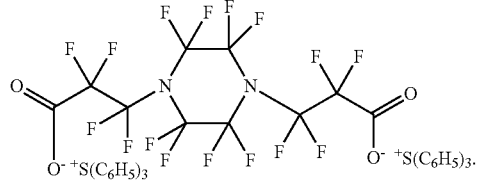

(5)

5. The composition of claim 1, wherein the at least one PDB is asymmetrical and has at least one structure selected from the group consisting of Structures 7-10:

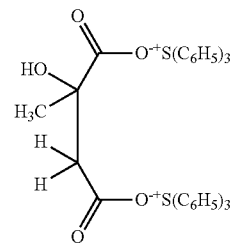

(7)

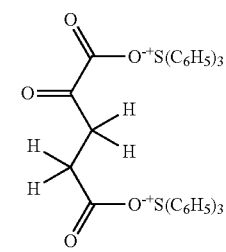

(8)

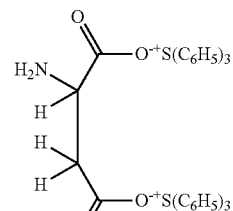

(9)

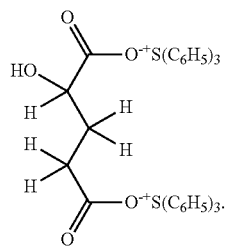

(10)

6. The composition of claim 1, wherein the resist polymer is selected from the group consisting of poly(p-hydroxystyrene)-methyl adamantyl methacrylate (PHS MAdMA) and poly(p-hydroxystyrene)-2-ethyl-2-adamantyl methacrylate (PHS EAdMA).

7. The composition of claim 1, further comprising a photoacid generator (PAG).

8. The composition of claim 7, wherein the PAG is selected from the group consisting of sulfonium salts, halonium salts, α,α'-bis-sulfonyl-diazomethanes, trifluoromethanesulfonate esters of imides, trifluoromethanesulfonate esters of hydroxyimides, nitrobenzyl sulfonate esters, sulfonyloxynaphthalimides, pyrogallol derivatives, alkyl disulfones, s-triazine derivatives, and sulfonic acid generators.

9. The composition of claim 8, wherein the PAG is the sulfonium salt triphenylsulfonium perfluorobutanesulfonate.

10. A method of patterning a substrate comprising the steps of:
(a) applying, over a substrate, a photoresist comprising the composition of claim 1, and a photoacid generator (PAG);
(b) post-application baking of the photoresist;
(c) exposing the photoresist to radiation;
(d) post-exposure baking of the photoresist; and
(e) developing the exposed resist with an aqueous base solution.

11. The method of claim 10, wherein the substrate is selected from the group consisting of a metal conductor layer, a ceramic insulator layer, and a semiconductor wafer.

12. The method of claim 10, wherein the photoresist is exposed with radiation selected from the group consisting of DUV optical radiation, ion-beam projection, x-ray radiation, electron beam (e-beam) radiation, focused beam radiation, and EUV radiation.

13. A composition comprising:
at least one dicarboxylate anion photodecomposable base (PDB) having at least one structure selected from the group consisting of Structures 3, 4, and 6:

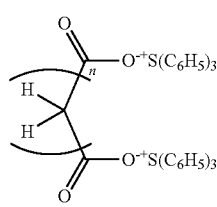
(3)

wherein n is 1, 3, or 4

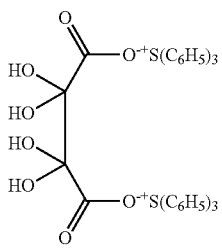
(4)

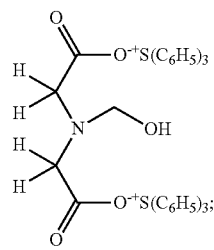
(6)

a resist polymer;
and pinane acetate p-toluenesulfonate as an acid amplifier.

14. The composition of claim 13, wherein the resist polymer is selected from the group consisting of poly(p-hydroxystyrene)-methyl adamantyl methacrylate (PHS MAdMA) and poly(p-hydroxystyrene)-2-ethyl-2-adamantyl methacrylate (PHS EAdMA).

15. The composition of claim 13, further comprising a photoacid generator (PAG).

16. The composition of claim 15, wherein the PAG is selected from the group consisting of sulfonium salts, halonium salts, α,α'-bis-sulfonyl-diazomethanes, trifluoromethanesulfonate esters of imides, trifluoromethanesulfonate esters of hydroxyimides, nitrobenzyl sulfonate esters, sulfonyloxynaphthalimides, pyrogallol derivatives, alkyl disulfones, s-triazine derivatives; and sulfonic acid generators.

17. The composition of claim 16, wherein the PAG is the sulfonium salt triphenylsulfonium perfluorobutanesulfonate.

18. A method of patterning a substrate comprising the steps of:
(a) applying, over a substrate, a photoresist comprising the composition of claim 13, and a photoacid generator;
(b) post-application baking of the photoresist;
(c) exposing the photoresist to radiation;
(d) post-exposure baking of the photoresist; and
(e) developing the exposed resist with an aqueous base solution.

19. The method of claim 18, wherein the substrate is selected from the group consisting of a metal conductor layer, a ceramic insulator layer, and a semiconductor wafer.

20. The method of claim 18, wherein the photoresist is exposed with radiation selected from the group consisting of DUV optical radiation, ion-beam projection, x-ray radiation, electron beam (e-beam) radiation, focused beam radiation, and EUV radiation.

21. A composition comprising at least one dicarboxylate anion photodecomposable base (PDB) comprising bis(triphenylsulfonium) tetrafluorodiglycolic acid (BisTPS TFDGA).

22. The composition of claim 21, further comprising a resist polymer.

23. The composition of claim 22, wherein the resist polymer is selected from the group consisting of poly(p-hydroxystyrene)-methyl adamantyl methacrylate (PHS MAdMA) and poly(p-hydroxystyrene)-2-ethyl-2-adamantyl methacrylate (PHS EAdMA).

24. The composition of claim 22, further comprising a photoacid generator (PAG).

25. The composition of claim 24, wherein the PAG is selected from the group consisting of sulfonium salts, halonium salts, α,α'-bis-sulfonyl-diazomethanes, trifluoromethanesulfonate esters of imides, trifluoromethanesulfonate esters of hydroxyimides, nitrobenzyl sulfonate esters, sulfonyloxynaphthalimides, pyrogallol derivatives, alkyl disulfones, s-triazine derivatives, and sulfonic acid generators.

26. The composition of claim 25, wherein the PAG is the sulfonium salt triphenylsulfonium perfluorobutanesulfonate.

27. The composition of claim 22, further comprising an acid amplifier.

28. The composition of claim 27, wherein the acid amplifier is pinane acetate p-toluenesulfonate.

29. A composition comprising at least one dicarboxylate anion photodecomposable base (PDB), wherein the PDB has a structure selected from the group consisting of Structures (1), (4)-(7), (9) and (10):
(1)
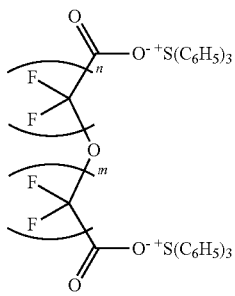
wherein n is 1, 2, or 3 and m is 1, 2, or 3
(4)
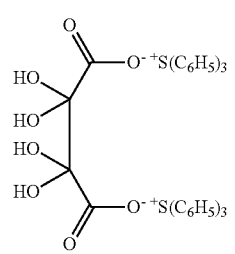
(5)
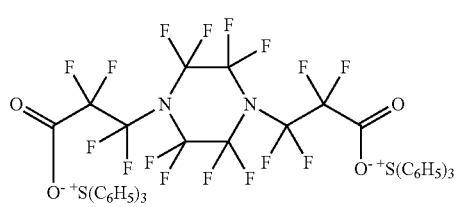
(6)
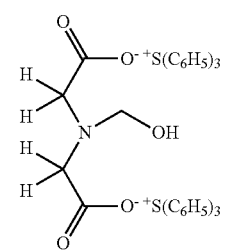
(7)
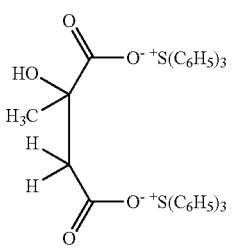
(9)
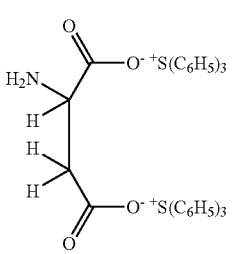
(10)
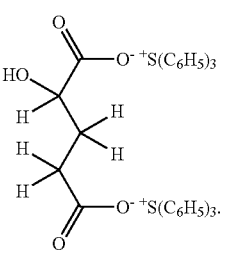
* * * * *